United States Patent
Hanson et al.

(10) Patent No.: US 8,140,349 B2
(45) Date of Patent: Mar. 20, 2012

(54) DRUG DELIVERY DEVICE INCORPORATING A TRACKING CODE

(75) Inventors: Robert Hanson, Mobile, AL (US); Barry Sudduth, Central, SC (US); Don Detar, Lilburn, GA (US)

(73) Assignee: Merge eMed, Inc., Hartland, WI (US)

( * ) Notice: Subject to any disclaimer, the term of this patent is extended or adjusted under 35 U.S.C. 154(b) by 1161 days.

(21) Appl. No.: 09/997,962

(22) Filed: Nov. 29, 2001
(Under 37 CFR 1.47)

(65) Prior Publication Data
US 2002/0099334 A1    Jul. 25, 2002

Related U.S. Application Data

(60) Provisional application No. 60/253,911, filed on Nov. 29, 2000.

(51) Int. Cl.
*G06Q 50/00* (2006.01)

(52) U.S. Cl. ........... 705/2; 705/3; 700/214; 604/207; 604/131; 235/385; 235/375

(58) Field of Classification Search ............ 604/131, 604/189, 207; 235/375, 385; 700/214; 705/2, 705/3
See application file for complete search history.

(56) References Cited

U.S. PATENT DOCUMENTS

| | | | |
|---|---|---|---|
| 4,781,696 A | 11/1988 | Moulding, Jr. et al. | |
| 4,853,521 A * | 8/1989 | Claeys et al. | 235/375 |
| 4,857,716 A * | 8/1989 | Gombrich et al. | 235/375 |
| 4,978,335 A | 12/1990 | Arthur, III | |
| 5,078,683 A | 1/1992 | Sancoff et al. | |
| 5,207,642 A | 5/1993 | Orkin et al. | |
| 5,533,981 A * | 7/1996 | Mandro et al. | 604/208 |
| 5,569,212 A * | 10/1996 | Brown | 604/207 |
| 5,584,701 A * | 12/1996 | Lampotang et al. | 434/272 |
| 5,593,390 A * | 1/1997 | Castellano et al. | 604/187 |
| 5,611,051 A | 3/1997 | Pirelli | |
| 5,628,309 A * | 5/1997 | Brown | 600/310 |
| 5,643,212 A * | 7/1997 | Coutre et al. | 604/131 |
| 5,645,534 A * | 7/1997 | Chanoch | 604/189 |
| 5,651,775 A * | 7/1997 | Walker et al. | 604/207 |

(Continued)

FOREIGN PATENT DOCUMENTS

CA    2403384    9/2001

(Continued)

OTHER PUBLICATIONS

Dialog search results.*

(Continued)

*Primary Examiner* — Dilek Cobanoglu
(74) *Attorney, Agent, or Firm* — Michael Best & Friedrich LLP (57) ABSTRACT

A tracking code is adhered to a syringe label cradle for tracking each activity regarding the syringe label cradle, e.g., drug preparation, drug inventory, drug dispensing, drug administration, drug return, drug charges, etc. The tracking code may be in the form of bar or other machine readable code, as well as human readable indicia. The unique tracking code enables tracking of events pertaining to a specific syringe from the time of being prepared with a prescribed drug to its disposal or return to a hospital pharmacy. A log is created relating the patient to the specific drug used and all information inputted with respect to the tracking code.

25 Claims, 4 Drawing Sheets

U.S. PATENT DOCUMENTS

| | | | | |
|---|---|---|---|---|
| 5,690,618 | A * | 11/1997 | Smith et al. | 604/232 |
| 5,692,640 | A * | 12/1997 | Caulfield et al. | 221/70 |
| 5,697,916 | A * | 12/1997 | Schraga | 604/207 |
| 5,704,922 | A * | 1/1998 | Brown | 604/207 |
| 5,716,345 | A * | 2/1998 | Halbich | 604/207 |
| 5,720,733 | A * | 2/1998 | Brown | 604/207 |
| 5,772,443 | A * | 6/1998 | Lampotang et al. | 434/272 |
| 5,781,442 | A * | 7/1998 | Engleson et al. | 700/214 |
| 5,782,814 | A * | 7/1998 | Brown et al. | 604/207 |
| 5,792,117 | A * | 8/1998 | Brown | 604/207 |
| 5,807,336 | A | 9/1998 | Russo et al. | |
| 5,845,264 | A | 12/1998 | Nelhaus | |
| 5,882,338 | A | 3/1999 | Gray | |
| 5,883,370 | A * | 3/1999 | Walker et al. | 235/375 |
| 5,925,021 | A * | 7/1999 | Castellano et al. | 604/207 |
| 5,928,201 | A * | 7/1999 | Poulsen et al. | 604/208 |
| 5,954,700 | A | 9/1999 | Kovelman | |
| 6,021,392 | A * | 2/2000 | Lester et al. | 705/2 |
| 6,032,155 | A | 2/2000 | de la Huerga | |
| 6,070,761 | A * | 6/2000 | Bloom et al. | 222/81 |
| 6,094,642 | A | 7/2000 | Stephenson et al. | |
| 6,170,746 | B1 * | 1/2001 | Brook et al. | 235/385 |
| 6,485,465 | B2 * | 11/2002 | Moberg et al. | 604/154 |
| RE38,189 | E * | 7/2003 | Walker et al. | 604/207 |
| 6,685,678 | B2 * | 2/2004 | Evans et al. | 604/207 |
| 2001/0049608 | A1 * | 12/2001 | Hochman | 705/3 |
| 2001/0056258 | A1 * | 12/2001 | Evans | 604/131 |
| 2002/0099334 | A1 * | 7/2002 | Hanson et al. | 604/189 |
| 2004/0082918 | A1 * | 4/2004 | Evans et al. | 604/207 |

FOREIGN PATENT DOCUMENTS

WO     WO 99/11306     3/1999

OTHER PUBLICATIONS

Google patents search results.*

Alan F. Merry. Craig S. Webster, and Daniel J. Matthew, *A New, Safety-Oriented, Integrated Drug Administration and Automated Anesthesia Record System*, Society for Technology in Anesthesia, 2001, pp. 385-390.

* cited by examiner

DRUG DELIVERY DEVICE INCORPORATING A TRACKING CODE

CROSS REFERENCE TO RELATED APPLICATIONS

The present application claims the benefit of U.S. Provisional Application No. 60/253,911, filed Nov. 29, 2000, the disclosure of which is hereby incorporated by reference herein.

BACKGROUND OF THE INVENTION

The present invention relates in general to a drug delivery system, and more particularly, to a unique tracking code associated with a medical device for use in drug delivery to a patient which enables the creation and retrieval of a data log relating the patient to the specific drug associated with the medical device and all patient and drug information/data stored in the system in association with the tracking code by the physician or other health care professional.

Manual dispensing of drugs from a hospital pharmacy for administration to a patient is a common practice in hospitals and other surgical facilities. Pharmacy departments generally fill syringes with drugs, the drugs being administered to the patient with the documenting of the drug handling process being performed in a retrospective manner using handwritten entries by the physician or other health care professional. The likelihood of human imperfection makes drug diversion, medication errors, errors of admission, medication contamination and inadvertent needle sticks a constant companion to drug administration. Additionally, the process is exacerbated by emergency situations which demand hurried setup and administration of drugs, with concurrently less time to pay attention to timely and accurate record keeping. In the end, there is generally no complete record regarding the history of the syringe from the time of being filled to the time of its disposal or return to the pharmacy.

Walker, et al., U.S. Pat. No. 5,651,775, assigned to the same assignee of the present application, which is incorporated herein by reference, discloses a drug delivery and monitoring system whereby drugs are safely delivered to a patient, monitored in real time during delivery and crucial events are recorded during delivery to provide on-line information and details for an audit trail. The basic components of the drug delivery and monitoring system include a scanning module, a syringe label cradle, a cassette tray and a drug injection port. The syringe label cradle is designed as a holder and positioner for a drug containing syringe. The syringe label cradle is constructed in a plurality of sizes to accommodate varying sizes of syringes to provide a constant needle height of the combined unit independent of the syringe volume, i.e., syringe barrel diameter. The syringe is positioned within the cradle and preferably securely affixed thereto by a self adhesive, preprinted label. The label provides drug identification indicia and drug preparation information such as drug dosage and concentration which can be in the form of human and/or machine readable indicia such as bar code and the like. The information on the label is automatically read into the system from the label using, for example, an optical bar code scanning module.

A plurality of syringe label cradle units, i.e., combination syringe label cradle and syringe, are placed within a cassette tray for transport and storage prior to, during and after use. Generally, the cassette tray is organized to hold the syringe label cradles and drug loaded syringe in a logically progressive array. In use, the cassette tray is aligned with the injection port which is most commonly connected to a patient-connected needleless IV injection set. The scanning module incorporates bar code or other digital indicia scanners to read the labels affixed to the syringe label cradle. Information contained on the label is in the nature of a code identifying, for example, the drug contained in an associated syringe, size of the syringe, syringe type, preparer of the drug and any expiration date associated with the drug. The scanning module also is used to monitor the syringe plunger movement as the drug is administered, thus acquiring drug administration dynamics in real-time, i.e., determining delivery rate and volume of administered drugs.

There is the desirability for further improvements in a drug administration system which provides a variety of medical devices, e.g., preloaded syringes and IV ports, with machine readable and/or human readable coded information enabling the tracking and accurate recording of the event history of the medical device, e.g., in the case of a syringe from the time of being filled to the time of its disposal or return to the pharmacy.

SUMMARY OF THE INVENTION

The tracking code system of the present invention may be used for a variety of medical applications and devices including, but not limited to injected drugs as noted herein. Broadly, the term "medical device" as used herein means any syringe application, IV ports, pill containers, drug vials, drug ampules, non-injectable drugs and fluids, whether intravenously or otherwise, all of which can be monitored using the tracking code system of the present invention. Specifically, the present invention uses a tracking code associated with a syringe cradle label unit and/or a port cradle label unit as to be more fully described hereinafter.

As discussed in Walker, et al., the syringe label cradle (SLC) is a single use product constructed to hold a syringe that is specific by size and manufacturer. A family of SLCs has been developed for use with common syringes of standard sizes. The SLC and attached syringe which form a syringe cradle label unit are encoded with a patient-specific tracking code. By way of one example, the tracking code is in the form of a machine readable bar code. The bar coded SLC incorporates a unique numeric field of, for example, 22 characters. The encoding takes place in the pharmacy or other designated preparation area, and a bar code label is mounted on the SLC flange. The SLC is then matched with the appropriate standard syringe and placed in administration sequence in a cassette tray. The encoded SLC provides accurate drug delivery data and digital tracking.

The tracking code in the form of a bar code is computer generated utilizing a time stamp and drug identification information. Each activity in which the SLC participates, e.g., drug preparation, drug inventory, drug dispensing, drug administration, drug return, drug charge or credit, etc., will be recorded and related to the unique tracking code. The tracking code enables tracking of events pertaining to a specific syringe or other medical device such as an IV port attached to a patient. Each time an SLC is utilized to deliver a drug to a patient, a log is created relating the patient to the specific drug used and all information contained in the respective patient and drug data bases. Relating the data bases via the tracking code enables specific drug use to be tracked. This can prove useful in FDA drug recalls as well as in narcotic control and drug research, both of which are important areas of pharmacy practice. Federal and state law requires narcotic control. The host data base server retrieves the detailed stored information regarding the medication about to be administered, e.g., name, concentration, expiration date/time, technician preparer, etc. This information can reside on either the server itself or on a remote network server, i.e., Ethernet/network implementation.

In accordance with one embodiment of the present invention there is described a medical device for the administration of a drug, the device comprising a source of a drug to be administered to a patient, a holder for the source, and a tracking code operatively associated with the source.

In accordance with another embodiment of the present invention there is described a syringe label cradle unit comprising a syringe label cradle, a syringe attached to the cradle, and a tracking code affixed to at least one of the cradle and the syringe.

In accordance with another embodiment of the present invention there is described a port label cradle unit comprising a port label cradle, an IV port attached to the cradle, and a tracking code affixed to at least one of the cradle and the IV port.

In accordance with another embodiment of the present invention there is described a method for tracking data associated with a medical device adapted for the administration of a drug to a patient, the method comprising providing a source of a drug to be administered to a patient, associating a tracking code with the source, providing data associated with the drug to be administered, and storing the data in association with the tracking code.

In accordance with another embodiment of the present invention there is described a method for tracking data associated with a medical device adapted for the administration of a drug to a patient, the method comprising providing a source of a drug to be administered to a patient, affixing the source in a cradle, providing a label having a bar code corresponding to a tracking code affixed to at least one of the source and the cradle, identifying data associated with the drug and the patient, storing the data in association with the tracking code on a storage device, and retrieving the data from the storage device in response to the tracking code.

In accordance with another embodiment of the present invention there is described a system for tracking data associated with a medical device adapted for the administration of a drug to a patient, the device comprising a cradle, a source of a drug to be administered to a patient attached to the cradle, a tracking code associated with at least one of the cradle and the source, and a storage and retrieval device for storing and retrieving data related to the drug in association with the tracking code.

BRIEF DESCRIPTION OF THE DRAWINGS

The above description, as well as further objects, features and advantages of the present invention will be more fully understood with reference to the following detailed description of a drug delivery device incorporating a tracking code, when taken in conjunction with the accompanying drawings, wherein.

DETAILED DESCRIPTION OF THE PREFERRED EMBODIMENTS

In describing the preferred embodiments of the subject matter illustrated and to be described with respect to the drawings, specific terminology will be resorted to for the sake of clarity. However, the invention is not intended to be limited to the specific terms so selected and is to be understood that each specific term includes all technical equivalents which operate in a similar manner to accomplish a similar purpose.

Figure 1:
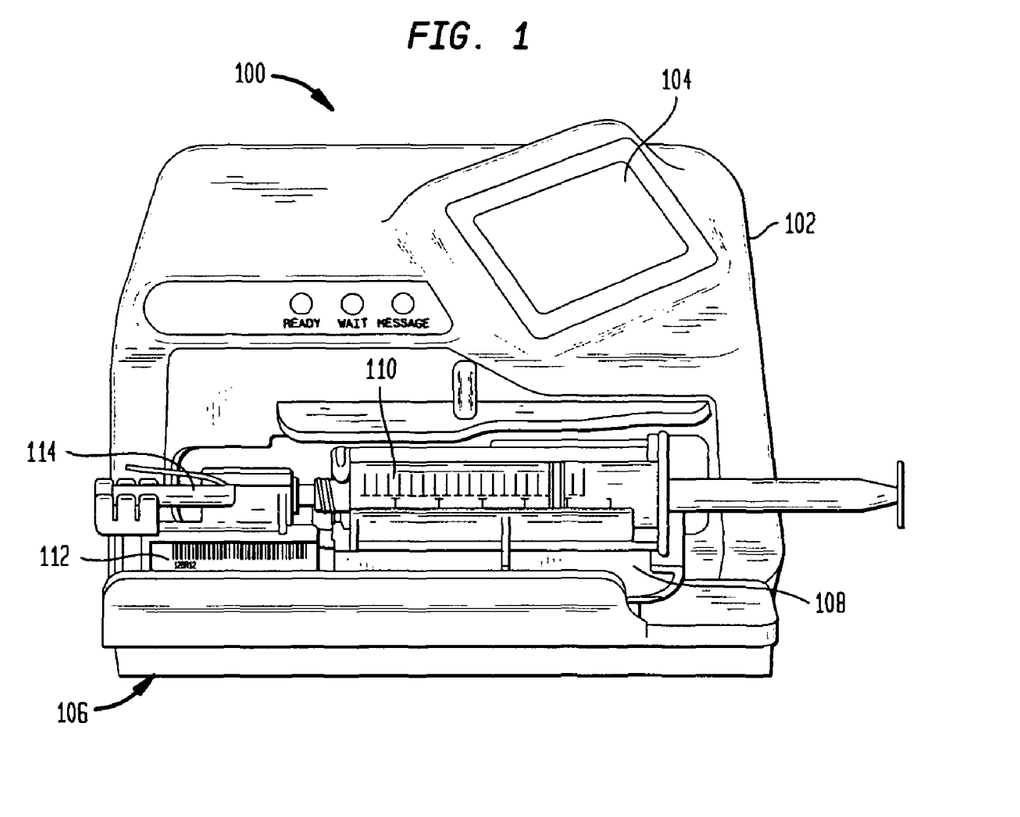
FIG. 1 is a perspective diagrammatic illustration of a drug administration and monitoring device using a syringe cradle label unit and a port cradle label unit associated with a tracking code in accordance with the present invention.

Referring to the drawings, wherein like reference numerals represent like elements, there is shown in FIG. 1 a drug administration and monitoring device generally designated by reference numeral 10. The device 10, as illustrated by way of one example, is a peripheral device for intravenous medication delivery that combines digital imaging and bar code scanning technologies. The device 10 automatically records drug delivery in real time and allows instant interaction with patient and drug data bases. This alerts the clinician before an impending adverse drug reaction or medication error can occur. A device 10 of the foregoing type is available from MedDoc, Inc. of Mobile, Ala. sold under the mark DocuJect.

The device 100 includes a housing 102 which contains the electronic components and other microelectronic modules, for example, a microprocessor, memory devices, input/output devices, etc. The housing 102 supports a display 104, for example, a liquid crystal display. The display 104 is functional to provide the physician or health care professional with the display of information and data during operation of the device 100. The device 100 includes a scanning module 106 containing an optical or other scanning device which removably supports in operative relationship a syringe label cradle (SLC) 108 to which there is attached a syringe 110 and a port label cradle (PLC) 112 to which there is attached a patient IV port 114. A detailed description of the basic construction, functions and operation of the device 100 in administering a drug from a syringe is more fully described in the aforementioned Walker, et al. patent.

Figure 2:
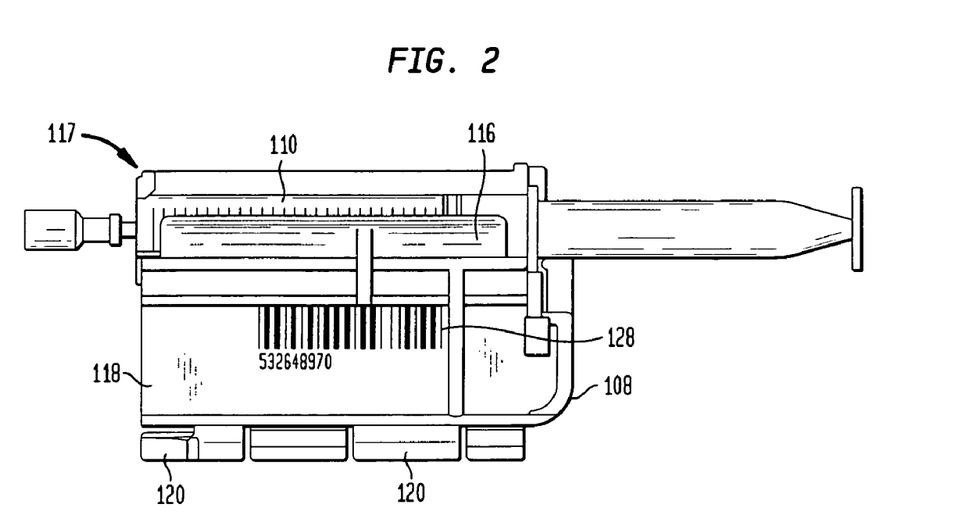
FIG. 2 is a front elevational view of a syringe cradle label unit having a label printed with a tracking code affixed to a flange of the cradle in accordance with one embodiment of the present invention.

As shown in FIG. 2, the SLC 108 is a single-use product designed to hold varying sizes of syringes 110. The syringe 110 is removably attached to the SLC 108 by means of a configured cradle 116. The combined SLC 108 and syringe 110 will be referred to hereinafter as the syringe label cradle unit (SLCU) 117. The SLC 108 includes a generally planar flange 118 supporting one or more slide engagement members 120. The slide engagement members 120 are received within a corresponding portion of the scanning module 106 permitting longitudinal movement of the SLC 108 within the scanning module, as well as positioning the needle of the syringe 110 into operative association with the patient's IV port 114. A more detailed description of the SLC 108 and SLCU 117 is described in the Walker, et al. patent, as well as in co-pending U.S. application Ser. No. 09/454,184 entitled, "Syringe For Use in a Drug Delivery System", filed on Dec. 3, 1999 in the name of Evans, et al. and assigned to the same assignee of the present application, the disclosures of which are incorporated herein by reference.

Figure 3:
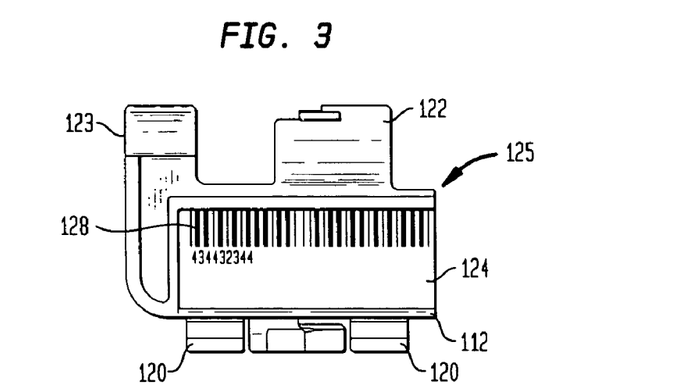
FIG. 3 is a front elevational view of a port cradle label unit having a label printed with a tracking code affixed to a flange of the cradle in accordance with one embodiment of the present invention.

Referring to FIG. 3, the PLC 112 includes a configured cradle 122 and IV tubing holder 123 which allows for the removable attachment of a patient IV port 114. The combined PLC 112 and IV port 114, and optionally the tubing holder 123 will referred to hereinafter as the port label cradle unit (PLCU) 125. The cradle 122 and tubing holder 123 are supported at one end of a planar flange 124 which is of similar construction to flange 118. One or more slide engagement members 126, similar to slide engagement members 120, are attached to the free end of flange 124. The slide engagement members 126 enable the PLC 112 to be longitudinally and slidingly received within the scanning module 106 in juxtaposition to the SLCU 117, see FIG. 1. The PLC 112 is a single-use product that secures the patient IV port 114 of the IV line in position to accept selected SLCUs 117 for drug injection. The PLC 112 also stabilizes the syringe 110 to provide an accurate and reliable reading of syringe plunger movement by the device 100. In a like manner, the SLC 108 stabilizes the syringe 110 in the appropriate position for accurate scanning of the syringe plunger movement for determining drug administration.

The PLC 112 assists in greatly reducing needle stick accidents by eliminating the need for clinicians to handle the injection port 114 of the IV line each time they inject a medication. The PLC 112 also affords protected IV access, thereby reducing contamination that may lead to nosocomial infections. A more detailed description of the construction and application of the PLC 112 with respect to the device 100 is described in co-pending U.S. application Ser. No. 09/813,547 entitled "Drug Delivery and Monitoring System" filed on Mar. 21, 2001 in the name of Evans and assigned to the same assignee of the present application, the disclosure of which is incorporated herein by reference.

The tracking code system of the present invention will now be described for illustrative purposes with reference to an SLCU 117 having an SLC 108 and syringe 110 for illustrative purposes. It is to be understood that the tracking code system can be adapted to other medical devices, such as the PLCU 125. In accordance with the present invention, the syringe 110 and the contained drug is associated with a tracking code which may be presented in machine and/or human readable form. By way of example, the tracking code may be in the nature of a bar code 128 which is readily readable by an optical scanner such as the scanning module 106. The tracking code may also be represented by human and machine readable alpha and numeric numbers and characters, as well as combinations thereof. The tracking code can be used for tracking all activities relating to a specific drug loaded syringe 110, for example, drug preparation, patient data, physician and pharmacist identification, diagnosis, date, drug inventory, drug dispensing, drug administration, drug return, drug credit or charge, etc. The tracking code can be associated with an electronic information and data log that relates the patient to the specific medication and drug data bases. The tracking code provides a useful tool in FDA drug recalls, as well as in narcotic control and drug research, as well as facilitating compliance with federal and state law requiring narcotic control.

The encoding of the SLCU 117 typically takes place in the pharmacy where a printed label containing the tracking code is applied to the flange 118 of the SLC 108. However, it is contemplated that the tracking code label can, in addition or in the alternative, be applied to the cradle 116 or directly to the syringe 110 if so desired. In lieu of a label, it is also contemplated that the tracking code can be printed directly on the flange 118, cradle 116 and/or syringe 110 using any suitable printing ink which will print and adhere to the polymer material of these components. By way of one embodiment, the tracking code is in the nature of a unique numeric field of 22 characters presented as a machine readable bar code. In addition to the tracking code, other bar coded information may be provided on the label which can be read by the scanning module 106. For example, the additional information can provide direct identification of drug name, drug concentration, patient name, hospital billing information, pharmacist's name, date of filling the syringe, drug administration information, etc. This additional bar coded information is further described in the Walker, et al. patent. In a similar manner, a tracking code and other bar code or other form of machine readable information may be applied to the PLC 112 for a similar purpose.

Figure 4A:
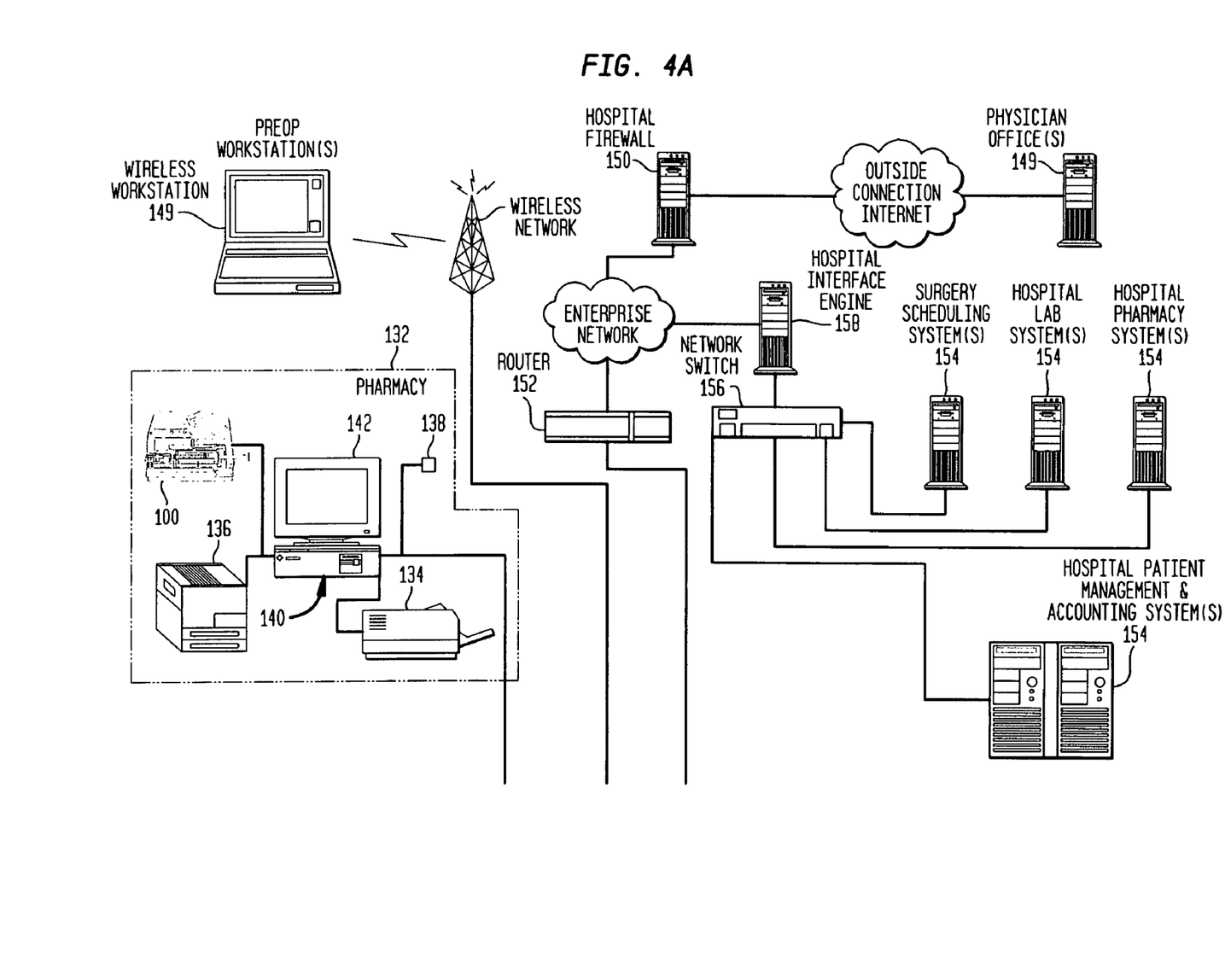
FIG. 4 is a diagrammatic illustration of a medical data and information storage and retrieval system embodying a medical device incorporating a medical device having a tracking code in accordance with one embodiment of the present invention.
Figure 4B:
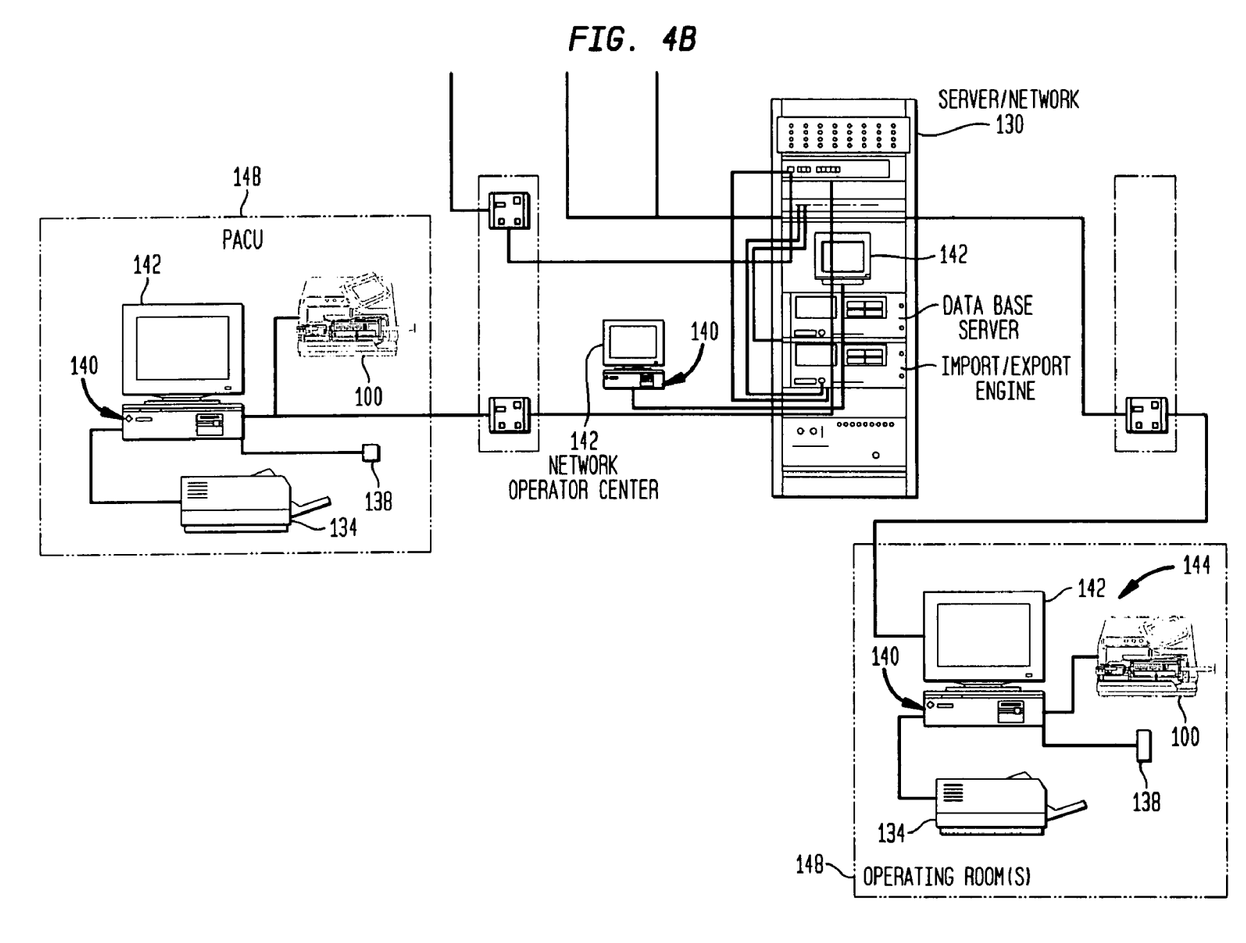

Referring to FIG. 4, there is diagrammatically illustrated an integrated network system as one example of one application of the use of a tracking code in accordance with one embodiment of the present invention. The network system is centered around a data base network server 130 such as those commercially known in the industry for the storage and retrieval of large amounts of information and data received and accessed from multiple locations. A physician or other health care professional, after ascertaining the need for one or more drugs, places an order for same by any suitable means with a pharmacy. The prescription is filled at a pharmacy work station 132 which includes a printer 134, a bar code label printer 136, a bar code scanner 138 and a drug administration device 100, all of which are connected to a desktop computer 140 including a touch screen monitor 142. The pharmacy workstation 132 also includes a supply of SLCs 108, syringes 110 of various sizes, vial/ampule kits and standardized drug trays. The drug tray is used for transport and secure storage of the prefilled, labeled SLCU 117, and drug vial/ampule kits.

The pharmacy workstation 132 facilitates preparation, e.g., loading, labeling and documentation of the prefilled syringes 110 and bar coded SLCs 108 and drug vial/ampule kits in a controlled, clean environment. The bar coded label may be scanned using the bar code scanner 138 to associate the tracking code with specific patient information stored on the data base server 130 which was entered by the pharmacists using the computer 140. Similarly, drug information such as drug name, concentration, time of preparation, etc. can also be associated with the tracking code by entering same into the data base server 130 under the tracking code. This is the first step in the creation of a medication administration record during the peri-operative process using the tracking code.

For each drug to be administered, the pharmacist prepares a kit containing the drug and an SLC 108 with a label printed with the unique tracking code. The kit may also include a syringe 110 of the appropriate size. A storage cart, for example an anesthesia cart, is filled with drug kits that have been prepared by the pharmacist. The anesthesia cart can be delivered to the particular location of drug administration, for example, operating rooms, patient anesthesia care units and the like. The physician will remove a drug kit from the anesthesia cart and prepare the medication by drawing up the drug into the appropriately sized syringe 110. The syringe 110 will be placed into the SLC 108 which has been previously labeled with the appropriate tracking code. The SLCU 117 can now be inserted into the drug administration device 100 for reading the tracking code and for administering the drug to the patient through, for example, an IV port 114 in the manner described in Walker, et al. and the '547 Application.

The tracking code is now attached to a specific SLCU 117 and is associated with a specific patient and syringe 110, which information is entered into the data base server 130 as if the SLCU had been originally prepared by the pharmacist at the pharmacy workstation 132. It is also contemplated that the SLCU 117 may be prepared by the pharmacist at the pharmacy workstation 132 and provided to the physician for drug administration to the patient using the drug administration device 100. In either event, the SLCU 117 will be identified by a unique tracking code. In preparing the SLC 108 or SLCU 117, the pharmacist or other health care professional enters into the data base server 130 relevant data which is associated with the tracking code. For example as previously noted, patient information, drug name, concentration, volume, date, pharmacist's name, hospital name, time, physician name, and any other desired information may be entered into the data base, e.g., into the data base network server 130. This information may be entered by means of the computer 140 or any other suitable data input device.

The SLCU 117 is adapted for administration of a drug to a patient through the patient IV port 114. Drug administration may occur, for example, in an operating room 144, a post anesthesia care unit 146 (PACU), or other location intended for drug administration. The operating room 144 or PACU 146 are equipped with a drug administration system 148 each including a drug administration device 100, a bar code scanner 138, a printer 134, a computer 140 and monitor 142. As shown, the pharmacy workstation 132, operating room 144 and PACU 148 are connected to the data base server 130 by any suitable means, such as an internal network system. However, it is also contemplated that communication with the data base server 130 may be accomplished by any suitable means, for example, a wireless preop workstation 149, such as using infrared, microradio communications and the like. It is further contemplated that the drug administration system 148 can be made portable such as on a self-contained utility cart which can be moved about, for example, from patient room to patient room or other locations as noted above where the drug administration system 148 is intended to be used.

The SLCU 117 and PLCU 125 are inserted into the drug administration device 100 which allows the bar code corresponding to the tracking code or other bar coded information to be read. The tracking code queries the data base server 130 to identify the syringe 110 and IV port 114, which may also include, for example, drug name, patient name, concentration, volume, date, pharmacist, etc. as well as information about possible adverse drug events. This information can be returned and generally displayed on the monitor 142 or display 104. At this time, the physician can dispense the drug from the syringe 110 whose needle has been inserted into the IV port 114. As the syringe plunger is depressed, the drug administration device 100 will monitor drug administration in real time as described in the Walker, et al. patent. The drug delivery information, i.e., quantity and time of delivery, can be automatically uploaded to the data base server 130 and stored along with the information which is associated with the tracking code for the SLCU 117 and/or PLCU 125. When completed, the SLCU 117 can be returned to the pharmacy workstation 132 for disposal of the returned drug. At this point, it is possible to verify the returned volume remaining in the syringe 110 against the automatically recorded dose given by the physician which is identified under the tracking code for the SLCU 117.

The physician or other health care professional can access data from the data base network server 130 from any one of a number of remote locations, for example, the pharmacy workstation 132, operating room 144, PACU 148, etc. By entering the unique tracking code, all information entered and associated with the tracking code can be displayed on the monitor 142 and printed to obtain a permanent record. The data base network server 130 may be accessed by other than through use of the drug administration system 148. For example, a physician in his office 149 either at the hospital or off-site may access the data base network server 130 through a hospital firewall 150 which is connected to the data base server through a router 152. The physician may access the data base network server 130 via the Internet, telephone modem or other suitable communications links.

In a similar way, other hospital computer management systems 154, for example, a surgical scheduling system, hospital lab system, hospital pharmacy system, hospital patient management and accounting system, etc. can be connected to the data base server 130 through a network switch 156 which is connected to a hospital interface engine 158. Accordingly, data to and from the data base server 130 may be accessed from a variety of remote locations by entering the unique tracking code. By inputting the tracking code, all information entered into the data base network server 130 relating to the tracking code which corresponds to an SLCU 117 or PLCU 125 can be retrieved. Thus, the history of the SLCU 117 from its birth in the pharmacy workstation 132 to its return to the pharmacy workstation can be monitored at any time during the life cycle of the SLCU. The physician or other health care provider need only enter the unique tracking code to obtain a real time report as to all events that have taken place with respect to the SLCU 117 or PLCU 125 and all data and information which have been related to the tracking code.

Although the invention herein has been described with reference to particular embodiments, it is to be understood that the embodiments are merely illustrative of the principles and application of the present invention. It is therefore to be understood that numerous modifications may be made to the embodiments and that other arrangements may be devised without departing from the spirit and scope of the present invention as defined by the claims.

What is claimed is:

1. A method for tracking event data associated with a medical device adapted for the administration of a drug to a patient, said method comprising:

generating a unique tracking code for a single medical device loaded with a drug, wherein said unique tracking code uniquely identifies said single medical device loaded with a drug such that said unique tracking code is different from each tracking code assigned to other medical devices loaded with said drug, receiving event data associated with said single medical device loaded with a drug, the received event data including information associated with an action performed relating to the single medical device loaded with a drug, the action including at least one of preparing the single medical device loaded with a drug, administering the single medical device loaded with a drug to a patient, and disposing of the single medical device loaded with a drug, storing the event data on a storage device with the unique tracking code for the single medical device loaded with a drug to form at least one record uniquely tied to the single medical device loaded with a drug, wherein the at least one record is different from each record created for the other medical devices loaded with said drug, receiving a request for information regarding the single medical device loaded with a drug, the request including said unique tracking code, retrieving stored event data from the at least one record including said unique tracking code stored on said storage device, and outputting the stored event data in response to the request.

2. The method of claim 1, further comprising outputting said tracking code to at least one printer for printing said tracking code as a bar code.

3. The method of claim 2, further including scanning said bar code for identifying said drug associated with said bar code prior to administration of said drug to a patient.

4. The method of claim 1, further including affixing said single medical device loaded with a drug to a cradle.

5. The method of claim 4, further including adhering a label containing said tracking code to at least one of said cradle and said single medical device loaded with a drug.

6. The method of claim 4, wherein said cradle comprises a syringe label cradle.

7. The method of claim 4, wherein said cradle comprises a port label cradle.

8. The method of claim 1, wherein said medical device comprises a syringe.

9. The method of claim 1, wherein said medical device comprises an IV port.

10. The method of claim 1, wherein said unique tracking code is stored in said storage device in associated with the identification of a patient to be administered said drug.

11. A method for tracking data associated with a medical device adapted for the administration of a drug to a patient, said method comprising:
preparing a single source of a drug to be administered to a patient, wherein said single source of a drug includes an individual drug and an individual medical device,
affixing said single source in a cradle,
providing a label having a bar code corresponding to a unique tracking code affixed to at least one of said source and said cradle, wherein said unique tracking code uniquely identifies said single source such that said unique tracking code is different from each tracking code assigned to other single sources of said drug,
identifying data associated with a first quantity of said drug in said single source and said patient,
storing said data in association with said unique tracking code on a storage device,
administering a second quantity of said drug to said patient from said single source,
disposing of said single source after administration of said drug to said patient;
updating said first quantity of said drug stored in the storage device with the unique tracking code based on the second quantity of said drug, and
retrieving said data from said storage device using said unique tracking code,
wherein said data, retrieved by the tracking code from the storage device, tracks said source from preparation of said source containing said drug to disposing of said source, wherein said unique tracking code conveys no information other than the identity of the tracking code.

12. The method of claim 11, wherein said medical device comprises a syringe.

13. The method of claim 11, wherein said medical device comprises an IV port.

14. The method of claim 11, wherein said tracking code identifies a single source associated with a single patient.

15. The method of claim 11, wherein said unique tracking code is stored in said storage device in associated with the identification of a patient to be administered said drug.

16. A method for tracking data associated with a medical device adapted for the administration of a drug to a patient, said method comprising:
preparing a single source of a drug to be administered to a patient, wherein said single source of a drug includes a drug and an individual syringe,
associating a unique tracking code with said single source, wherein the unique tracking code uniquely identifies the single source such that the unique tracking code is different from each tracking code assigned to other single sources loaded with the drug,
providing first data associated with said tracking code relating to said drug in said single source to be administered,
providing second data representing an amount of said drug in said single source administered to said patient from said single source associated with said tracking code,
providing third data associated with disposing of said single source,
storing said first, second, and third data in association with said tracking code on a storage device,
retrieving said first, second, and third data from said storage device using said tracking code,
whereby said first, second, and third data associated with said tracking code and retrieved by the tracking code from the storage device, tracks the preparing of said source, the administration of said drug in said source to a patient, and said disposal of said source.

17. The method of claim 16, wherein said unique tracking code is stored in said storage device in associated with the identification of a patient to be administered said drug.

18. The method of claim 16, wherein said unique tracking code conveys no information other than the identity of the tracking code.

19. A method for tracking data associated with a medical device adapted for the administration of a drug to a patient, said method comprising:
providing a single source of a drug to be administered to a patient, wherein said single source of a drug includes a drug and an individual syringe,
associating a unique tracking code with said single source, wherein said unique tracking code uniquely identifies said single source such that the unique tracking code is different from each tracking code assigned to other single sources of said drug,
providing data associated with said single source from providing of said single source to disposal of said single source,
storing said data in association with said tracking code on a storage device, whereby the stored data may be altered while still being associated with the same unique tracking code, and
retrieving the stored data from said storage device using said tracking code,
wherein the stored data retrieved by the tracking code from the storage device, tracks the single source from the providing of said source to the disposal of said source.

20. The method of claim 19, wherein said unique tracking code is provided on a bar code and the bar code is affixed to the single source.

21. The method of claim 20, wherein said single source includes other markings other than said bar code containing said unique tracking code.

22. The method of claim 21, wherein said other markings comprises written text, type written text, patient information, drug information, or other bar codes.

23. A method for tracking data associated with a medical device adapted for the administration of a drug to a patient, said method comprising:

preparation of a single source of a drug to be administered to a patient, wherein said single source of a drug includes a drug and an individual syringe, affixing said single source in a cradle, providing a label having a bar code corresponding to a unique tracking code, wherein said label is affixed to at least one of said source and said cradle, and wherein said unique tracking code uniquely identifies said single source such that the unique tracking code is different from each tracking code assigned to other single sources of said drug, identifying data associated with said drug in said single source and said patient, storing said data in associated with said unique tracking code on a storage device, administering a quantity of said drug contained in said source to a patient, disposing of said single source after administration of said drug to a patient, updating said data in association with the unique tracking code on said storage device, and retrieving said data from said storage device using said unique tracking code, wherein said data, retrieved by the tracking code from the storage device, tracks said source from preparation of said source containing said drug to disposing of said source, wherein said unique tracking code conveys no information other than the identity of the tracking code.

24. The method of claim 23, wherein said single source includes other markings than said unique tracking code.

25. The method of claim 24, wherein said other markings comprises written text, type written text, patient information, drug information, or other bar codes.

* * * * *